United States Patent

Farng et al.

[11] Patent Number: 5,578,556
[45] Date of Patent: Nov. 26, 1996

[54] TRIAZOLE-MALEATE ADDUCTS AS METAL PASSIVATORS AND ANTIWEAR ADDITIVES

[75] Inventors: Liehpao O. Farng, Lawrenceville; Andrew G. Horodysky, Cherry Hill; Ronald J. Poole, Mullica Hill, all of N.J.

[73] Assignee: Mobil Oil Corporation, Fairfax, Va.

[21] Appl. No.: 564,462

[22] Filed: Nov. 30, 1995

[51] Int. Cl.⁶ ................................. C10M 133/44
[52] U.S. Cl. ................................................. 508/231
[58] Field of Search ............... 252/51.5 A, 51.5 R, 252/48.6, 47.5

[56] References Cited

U.S. PATENT DOCUMENTS

| | | | |
|---|---|---|---|
| 3,969,237 | 7/1976 | Andress, Jr. | 252/51.5 A |
| 4,048,082 | 9/1977 | Nnadi et al. | 252/51.5 A |
| 4,153,565 | 5/1979 | Braid et al. | 252/51.5 A |
| 5,171,463 | 12/1992 | O'Neil | 252/51.5 A |
| 5,328,625 | 7/1994 | Farng et al. | 252/51.5 A |
| 5,362,411 | 11/1994 | Bergstra et al. | 252/51.5 A |

*Primary Examiner*—Jacqueline V. Howard
*Attorney, Agent, or Firm*—Ronald A. Bleeker; Malcolm D. Keen

[57] ABSTRACT

Triaole-dialkyl maleate derivatives have been found to be effective metal passivators and antiwear additives for lubricants and fuels.

11 Claims, No Drawings

TRIAZOLE-MALEATE ADDUCTS AS METAL PASSIVATORS AND ANTIWEAR ADDITIVES

FIELD OF THE INVENTION

This invention is directed to triazole-derived dialkyl maleate adducts with demonstrated abilities as metal passivators and antiwear additives for use as lubricity agents in lubricants and fuels.

BACKGROUND OF THE INVENTION

Triazole derivatives, such as benzotriazole, and 1,2,4-triazole have been used for their anti-corrosion, metal passivating properties as well as biological properties in a variety of lubricant applications, as disclosed in U.S. Pat. Nos. 4,791,206 and 4,456,539 and for fungicide/biocide applications. Tolyltriazole has corrosion inhibitor qualities as well as being a metal passivator. These patents are hereby incorporated herein by reference in their entireties. However, its use has been limited due to poor solubility in fuels and lubes.

Triazoles and their derivatives have been described as additives in lubricants and fuels. For example, U.S. Pat. No. 4,519,928 which issued to Braid discloses N-t-alkylated benzotriazoles as antioxidant and anticorrosion additives in lubricants. U.S. Pat. No. 4,060,491 issued to Bridger et al. discloses 5-alkylbenzotriazoles where the alkyl group contains from 4 to about 16 carbon atoms as antiwear additives in lubricants. U.S. Pat. No. 4,212,754 issued to Chibnik discloses Werner coordinated complexes prepared with benzotriazoles which may be used as antiwear additives in liquid hydrocarbon fuels.

U.S. Pat. No. 5,328,625 which issued to Farng et al. on Jul. 12, 1994 is directed to triazole-derived acid-ester or ester-amide-amine derivatives which are converted to their corresponding diester, amide-ester salts by reaction with amine, hydroxy or hydroxylamine compounds. This patent is hereby incorporated by reference herein.

Use of maleate esters in rubbers and plastics has been extensively reported as having beneficial flow-promoting properties as well as viscosity/friction reduction characteristics. They may function as spacers between the polymer molecules, and therefore, less energy is required for molecular bond rotation and polymers become capable of flow at temperatures below their decomposition temperature. Furthermore, they can lower the metal viscosity and change physical properties of the product such as increasing the softness and flexibility, and decreasing the cold flex temperature.

It is believed that none of the prior art patents disclose fuel or lubricant compositions containing the reaction products of aromatic triazoles and dialkyl esters of the present invention.

SUMMARY OF THE INVENTION

It has been found that lubricant and grease compositions containing small additive concentrations of triazole-dialkyl maleate reaction products possess excellent antiwear properties coupled with good metal passivating/anticorrosion activities. Additional cleanliness, antioxidant, extreme pressure, antifatigue, high temperature stabilizing, and friction modifying properties are also obtainable. Both the triazole moiety and the maleate ester moiety are believed to provide the basis for the synergistic antiwear and metal passivation properties of these novel additives. These additives can also be used in fuel compositions to provide many of the above properties when used in internal combustion engines. Concentrations in fuels can vary from 0.0001% to 0.2% by weight.

All of these beneficial properties are believed to be enhanced as a result of this novel internal synergism. This unique internal synergism concept is believed to be applicable to similar structures containing (a) triazole groups and (b) maleate ester groups within the same molecule. The products of this invention show good stability and compatibility when used in the presence of other commonly used additives in fuel or lubricant compositions.

It is therefore an object of this invention to provide for small concentrations of reaction products of tolyltriazole and dioctyl maleate which possess excellent lubricity and antiwear properties when incorporated into gasoline, diesel, and jet distillate fuels.

It is another object of this invention to provide for aryl triazole-dialkyl maleate products of reaction which contain in one molecule triazole and maleate ester groups to obtain a synergistic combination of antiwear/EP, metal passivation, corrosion inhibiting, and stability improving properties.

It is a further object of this invention to provide for reaction products which additionally impart extreme pressure (EP) activity, cleanliness, antioxidant, antifatigue, high temperature stabilizing, and friction modifying qualities to distillate fuels and lubricants.

It is yet another object of this invention to enhance the stability and compatibility of fuel and lubricant products containing small concentrations of these reaction products.

It is another further object of this invention to provide for small concentrations of reaction products mentioned above for incorporation into lubricants such as lube oils and greases to impart similar properties and qualities thereto.

It is a still further object of this invention to provide for small concentrations of the reaction products mentioned above for incorporation into liquid fuels, gasoline and diesel fuels to impart similar properties and qualities thereto.

DESCRIPTION OF THE PREFERRED EMBODIMENTS

It has now been found that the use of triazole-dialkyl maleate derivatives described herein provide unexpected, but exceptional antiwear/EP activity with significant metal passivating, corrosion inhibiting, and stability improving properties.

These remarkable benefits are also expected for a variety of synthetic and mineral oil based lubricants and light distillate fuels containing these additives. The compositions are believed to be novel and have not been previously used as antiwear/anticorrosion additives in lubricating oils, greases, or fuel applications.

Triazoles (benzotriazole, tolyltriazole, or 1,2,4-triazole, dodecylbenzotriazole, carboxybenzotriazole and 4,5,6,7-benzotriazole and mixtures thereof) were reacted with dialkyl maleates to form triazole-maleate adducts. Of these, tolyltriazole is preferred. Other $C_2$ to $C_{18}$ triazoles can be utilized herein. Aromatic triazoles are disclosed in U.S. Pat. No. 5,183,475 that issued to Cardis et al. on Feb. 2, 1993. This patent is hereby incorporated by reference herein.

Dialkyl esters which can be utilized herein include but are not limited to di-2-ethylhexyl maleate (dioctyl maleate), di-butyl maleate, di-isooctyl maleate, di-ethyl maleate, dimethyl maleate or other dialkyl esters having from 1 to about 124 carbon atoms therein and mixtures thereof. Of these, dioctyl maleate is preferred. Dioctyl maleate ester is mentioned as a plasticizer in U.S. Pat. No. 4,275,106 which issued to Watanabe on Jun. 23, 1981. This patent is incorporated by reference herein.

A diluent or solvent may be use, normally a $C_1$ to $C_4$ alcohol is utilized. Of these, 2-propanol is preferred. Other solvents which can be used herein include aromatic hydrocarbons such as toluols or xylenes and mixtures thereof.

The reaction proceeds as follows according to the equation below:

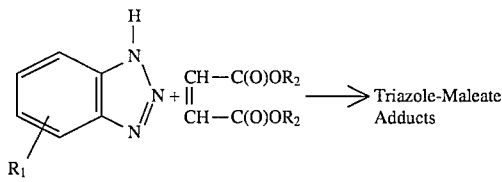

where $R_1$ is hydrogen or $C_1$ to $C_{12}$ hydrocarbyl or hydrocarbyloxyhydrocarbylene or mixture thereof; and where $R_2$ is $C_1$ to $C_{60}$ hydrocarbyl. $R_1$ or $R_2$ can optionally contain additional sulfur, oxygen and/or nitrogen.

These compositions can also be used in the presence of other commonly used additives in diesel fuel compositions. Use in other fuels such as gasoline and jet fuels are expected to provide similar results. The gasoline may contain oxygenated compounds such as alcohols or ethers. These compositions can also be used in lubricants to provide many of the same beneficial properties.

Generally speaking, conditions for the above described reactions may vary widely depending upon specific reactants, the presence or absence of a solvent and the like. Any suitable set of reaction conditions known to the art may be used. Generally, stoichiometric quantities of reactants are used. However, equimolar, more than molar or less than molar amounts may be used without detracting from the invention. An excess of up to 100% or more of any of the reactants can be used. In other words, more than molar quantities, or less than molar quantities, or almost equimolar quantities of triazoles or maleates can be used to make various compositions.

The reaction temperature may vary from ambient to about 177° C. (350° F.) or reflux, the pressure may vary from ambient or autogenous to about 500 psi. An initiating amount of an initiator such as azobisisobutyronitrile, isopropyl peroxydicarbonate, benzoyl peroxide, or a tertiary amine such as triethylamine or dimethyl cocoamine (ARMEEN DMCD) may also be utilized.

The additives embodied herein are utilized in lubricating oil or grease compositions in an amount which imparts significant antiwear characteristics to the oil or grease as well as reducing the friction of engines operating with the oil in its crankcase. Concentrations of about 0.001 to about 10 wt % based on the total weight of the composition can be used. Preferably, the concentration is from 0.1 to about 3 wt %.

The additives have the ability to improve the above noted characteristics of various oleaginous materials such as hydrocarbyl lubricating media which may comprise liquid oils in the form of either a mineral oil or a synthetic oil, or in the form of a grease in which the aforementioned oils are employed as a vehicle.

In general, mineral oils, both paraffinic, naphthenic and mixtures thereof, employed as the lubricant, or grease vehicle, may be of any suitable lubricating viscosity range, as for example, from about 45 SUS at 100° F. (37.8° C.) to about 6,000 SUS at 100° F. (37.8° C.) and preferably, from about 50 to about 250 SUS at 210° F. (98.9° C.). These oils may have viscosity indexes preferably ranging to about 95. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any material which is normally employed for thickening or gelling hydrocarbon fluids for forming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, synthetic liquid hydrocarbons such as the polyolefin derivatives, especially the hydrogenated polyolefins such as the polyisobutylenes, polybutenes, and the hydrogenated poly alpha-olefins (PAOs) including, especially, the hydrogenated polydecenes; the polyglycols or polyalkylene glycols (PAGs) such as polypropylene glycol and polyethylene glycol, synthetic esters such as the esters of dibasic aliphatic or aromatic carboxylic acids and monohydric alcohols such as di(2-ethylhexyl) sebacate, di(2-ethylhexyl) adipate and dibutyl phthalate and the esters of polyhydric alcohols and monobasic carboxylic acids such as the neopentyl polyol esters of monocarboxylic acids, including the neopentyl glycol, trimethylolpropane and pentaerythritol (mono- and di- pentaerythritol) esters of acids such as the $C_5$–$C_{20}$ monocarboxylic acids including the straight and branched chain acids, especially the $C_5$–$C_{12}$ straight and branched chain acids and mixtures of these acids. Synthetic lubricating fluids of these and other less common types such as the fluorocarbons, esters of phosphorus-containing acids, siloxanes and silicones (polysiloxanes), alkyl-substituted diphenyl ethers typified by a butyl-substituted bis(p-phenoxy phenyl) ether, and phenoxy phenylethers, are described in "Synthetic Lubricants" Gunderson & Hart, Reinhold Publ. Corp. 1962, to which reference is made for a description of these materials. Additional synthetic fluids or vehicles appear in U.S. Pat. Nos. 5,348,674 and 5,338,470 which issued to Blain et al. on Sept. 20, 1994 and to Hiebert et al. on Aug. 16, 1994, respectively. These patents are incorporated by reference herein in their entireties.

It is to be understood, however, that the compositions contemplated herein can also contain other materials. For example, corrosion inhibitors, extreme pressure agents, low temperature properties modifiers and the like can be used as exemplified respectively by metallic phenates or sulfonates, polymeric succinimides, non-metallic or metallic phosphorodithioates and the like. These materials do not detract from the value of the compositions of this invention, rather the materials serve to impart their customary properties to the particular compositions in which they are incorporated.

The additives in accordance with the invention are believed to be highly useful in fuel compositions, particularly in liquid hydrocarbon fuels or oxygenated fuels such as alcoholic fuels, ether-containing fuels, and the like and mixtures thereof. Exemplary alcoholic fuels may comprise gasoline containing methanol, ethanol, or propanol and mixtures thereof or ethers such as t-butylmethyl ethers. The present additives are used in fuel compositions in amounts ranging from about 1 to about 1,000 pounds of additive per 1,000 barrels of fuel and preferably from about 10 to about 250 pounds per 1,000 pounds of fuel. In addition to liquid hydrocarbon and oxygenated combustion fuels, distillate fuels and fuel oils are also contemplated. Additive concentration in these fuels vary from 0.0001 wt % to about 0.2 wt %.

The composition of this invention may also be used in conjunction with other fuel antiwear, detergent, cleanliness, low-temperature fluidity improving, octane improving, cetane improving, anticorrosion, antistaining, metal deactivating, combustion improving, antioxidant, fiction reducing, and demulsifying compositions.

The following examples are merely illustrative and are not meant to be limitations.

EXAMPLE 1

Reaction Product of Tolyltriazole and Dioctyl Maleate

Approximately 80.0 gm (0.6 mole) of tolyltriazole, 0.5 gm of azobisisobutyronitrile (AIBN, initiator), 100 ml 2-propanol, and 204.0 gm (0.6 mole) of di-2-ethylhexyl maleate (dioctyl maleate, commercially available from Aristech Chemical Corporation under the trade name, PX 538) were charged into a 1-liter reactor equipped with reflux condenser, thermometer, and mechanical agitator. This reaction mixture was heated to 192.6° F. (75° C.) and was held at that temperature for about for hours. Thereafter, the reaction temperature increased to 212° F. (100° C.) and volatile solvent was removed by vacuum distillation. Then, the reaction mixture was further reacted at a) 345.6° F. (160° C.) for one hour, b) 390.6° F. (185° C.) for four hours, and c) 453.6° F. (220° C.) for one hour. The viscous crude product was filtered hot to produce 284 gm of dark, brownish fluid.

EXAMPLE 2

Reaction Product of Tolyltriazole and Dioctyl Maleate

Approximately 80.0 gm (0.6 mole) of tolyltriazole and 204.0 gm (0.6 mole) of di-2-ethylhexyl maleate (dioctyl maleate, commercially available from Aristech Chemical Corporation under the trade name, PX 538) were charged into a 1-liter reactor equipped with reflux condenser, thermometer, and mechanical agitator. This reaction mixture was heated to 507.6° F. (250° C.) and was held at that temperature for about one hour. The viscous crude product was filtered hot to produce 282 gm of dark, brownish fluid.

EXAMPLE 3

Reaction Product of Tolyltriazole and Dibutyl Maleate

Approximately 133.0 gm (1.0 mole) of tolyltriazole and 228.0 gm 1.0 mole) of dibutyl maleate (commercially available from Aristech Chemical Corporation under the trade name, PX 504), were charged into a 1-liter reactor equipped with reflux condenser, thermometer, and mechanical agitator. This reaction mixture was heated to 417.6° F. (200° C.) and was held at that temperature for about two hours. The viscous crude product was filtered hot to produce 360 gm of dark, brownish fluid.

EXAMPLE 4

Reaction Product of Tolyltriazole and Dibutyl Maleate

Approximately 120.0 gm (0.9 mole) of tolyltriazole, and 229.0 gm (1.0 mole) of dibutyl maleate (commercially available from Aristech Chemical Corporation under the trade name, PX 504) were charged into a 1-liter reactor equipped with reflux condenser, thermometer, and mechanical agitator. This reaction mixture was heated to 417.6° F. (200° C.) and was held at that temperature for about four hours, and then the viscous crude product was filtered at hot to produce 348 gm of dark, brownish fluid.

The products of the above examples were blended into mineral oils and evaluated for antiwear performance using the Four-Ball test (Method D-2266, Table 1). See U.S. Pat. No. 4,761,482, incorporated herein by reference, for further details.

TABLE 1

| | Four-Ball Wear Test |
|---|---|
| Item | Wear Scar Diameter in MM 200° F. (93.3° C.), 40 Kg, Load, 1,800 rpm, 30 minutes |
| Base oil (80% solvent paraffinic bright, 20% solvent paraffinic neutral mineral oils) | 0.733 |
| 1% Example 1 in above oil | 0.444 |
| 1% Example 2 in above oil | 0.484 |
| 1% Example 3 in above oil | 0.511 |
| 1% Example 4 in above oil | 0.522 |

The products of the above examples were also blended into fully formulated industrial oils and evaluated for corrosion inhibition/thermal stability performance using the CMCo heat test (Table 2) developed by Cincinnati Milacron Co. The composition was tested for thermal stability and anticorrosion properties using a test procedure developed by Cincinnati Milacron Company. This test is described in U.S. Pat. No. 4,592,851 which issued to Stadtmiller, et al. on Jun. 3, 1986. This patent is hereby incorporated by reference herein.

The test procedure utilizes two clean weighed rods which are 0.25 of an inch in diameter and three inches long. One of rods is comprised of 99.9 percent copper and the other one is comprised of 1.0 percent carbon steel. The rods are submerged in 200 cc. of the test oil and remain in contact with each other as the oil is heated to 275° F. (135° C.). After being heated for 168 hours at 135° C., the rods are removed from the oil and any loose sludge is squeezed back into the oil. At this point the copper rod is visually evaluated and rated as to stain and discoloration by the ASTM D-130 rating scale.

The total volume of test oil is then evaluated for sludge in accordance with the Cincinnati Milacron test procedure. In this procedure the total amount of oil is filtered through a preweighed No. 41 Whatman filter paper. Any remaining residue found in the beaker is washed with naphtha onto the filter paper. The residue on the filter paper is washed with naphtha until all evidence of oil is removed from the residue. The residue and filter paper is air dried and then weighed. The weight of residue from 200 ml. of oil is determined by subtracting the original weight of filter paper from the weight of paper and residue. This weight is noted in the results below as sludge weight in mg./100 ml.

The results obtained from this composition were copper corrosion (ASTM) 2C, copper rod weight change mg. and sludge, mg./100 ml.

TABLE 2

$CMC_o$ Heat Test

| Item | Additive Conc. (wt %) | Copper 1 Week @ 275° F. (135° C.) | Steel 1 Week @ 290° F. (143° C.) |
|---|---|---|---|
| Base oil (formulated mineral oil containing defoamant/ demulsifier/antioxidant/ antiwear/dispersant performance package) | — | 9/1 | 10/1 |
| Example 1 in above oil | 0.03 | 3/1 | 4/1 |
| Example 3 in above oil | 0.03 | 3/1 | 3/1 |

The product of above example 2 was blended into diesel fuels and evaluated for antiwear performance using the Four-Ball test (Method D-2266, Table 3).

TABLE 3

Four-Ball Wear Test

| Item | Wear Scar Diameter in MM 122° F. (50° C.), 10 Kg, 600 rpm, 30 minutes |
|---|---|
| Base fuel (Refinery diesel) | 0.438 |
| 0.1% Example 2 in above fuel | 0.338 |

As shown above, the product of this invention shows very good antiwear characteristics as evidenced by the reaction of wear scar diameter in test results.

TEST RESULTS

Use of additive concentrations of triazole-maleate derivatives in premium quality industrial and automotive lubricants and diesel fuels will significantly enhance their stability, improve load-carrying, reduce wear and corrosion, and extend the service life of these lubricants. These additives also have the potential to benefit gasoline as well as other fuels by improving the antioxidation, antiwear, and anticorrosion characteristics of these fuels. These novel compositions described above are useful at low concentrations and do not contain any potentially undesirable metals or phosphorus. These multifunctional antiwear additives can be commercially made by using an economically favorable process which could be readily implemented using known technology in existing equipment.

Although the present invention has been described with preferred embodiments, it is to be understood that modifications and variations may be resorted to, without departing from the spirit and scope of this invention, as those skilled in the art will readily understand. Such variations and modifications are considered to be within the purview and scope of the appended claims.

What is claimed:

1. An improved lubricant composition comprising a major proportion of an oil of lubricating viscosity or grease prepared therefrom and a minor multifunctional antiwear, load-carrying/EP, metal passivating, corrosion inhibiting, and stability improving additive product of reaction prepared by reacting optionally in the presence of an initiator (a) an aryl triazole or a triazole with (b) a dialkyl ester where the aryl triazole has the following structure:

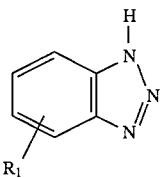

where $R_1$ is hydrogen or $C_1$ to $C_{12}$ hydrocarbyl or hydrocarbyloxyhydrocarbylene or mixture thereof; and where the dialkyl ester has the following structure:

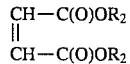

where $R_2$ is $C_1$ to $C_{60}$ hydrocarbyl; where $R_1$ and $R_2$ optionally contain a substituted heteroatom selected from a member of the group consisting of S, O, and N or a mixture thereof; and wherein the reaction is carried out at temperatures varying from ambient to about 350° C. under ambient or autogenous pressures, in molar ratios of reactants which vary from equimolar to more than molar to less than molar for a time sufficient to obtain the desired additive product of reaction.

2. The composition of claim 1 wherein the reaction is carried out as follows:

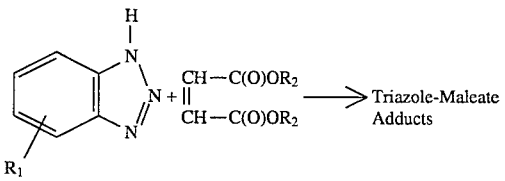

where $R_1$ is hydrogen or $C_1$ to $C_2$ hydrocarbyl or hydrocarbyloxyhydrocarbylene or mixture thereof; where $R_2$ is $C_1$ to $C_{60}$ hydrocarbyl; and where $R_1$ and $R_2$ optionally contain a substituted heteroatom selected from a member of the group consisting of S, O, and N or a mixture thereof.

3. The composition of claim 1 wherein the reactants are tolytriazole and dioctyl maleate along with an azobisisobutyronitrile initiator.

4. The composition of claim 1 wherein the reactants are dioctyl maleate and the aryl triazole comprises benzotriazole and the triazole is 1,2,4-triazole.

5. The composition of claim 1 wherein the lubricant is an oil of lubricating viscosity selected from the group consisting of (1) mineral oils, (2) synthetic oils, (3) or mixtures of mineral and synthetic oils or is (4) a grease prepared from any one of (1), (2) or (3).

6. The composition of claim 5 wherein the lubricant contains from about 0.001 to about 10 wt % based on the total weight of the composition of the additive product of reaction.

7. The composition of claim 5 wherein the lubricant is a mineral oil.

8. The composition of claim 1 wherein the reactants are tolytriazole and dibutyl maleate.

9. The composition of claim 1 wherein the reactants are benzotriazole and dioctyl maleate.

10. The composition of claim 1 wherein the reactants are benzotriazole and dibutyl maleate.

11. A method of preparing an improved lubricant composition comprising adding to said lubricant a minor multifunctional antiwear, load-carrying/EP, metal passivating, corrosion inhibiting, stability improving lubricant additive amount of from about 0.001 to about 10 wt % based on the total weight of the lubricant composition of an additive product of reaction prepared by reacting optionally in the presence of an initiator (a) an aryl triazole or a triazole with (b) a dialkyl ester where the aryl triazole has the following structure:

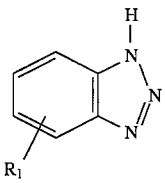

where $R_1$ is hydrogen or $C_1$ to $C_{12}$ hydrocarbyl or hydrocarbyloxyhydrocarbylene or mixture thereof; and where the dialkyl ester has the following structure:

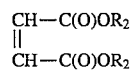

where $R_2$ is $C_1$ to $C_{60}$ hydrocarbyl; where $R_1$ and $R_2$ optionally contain a substituted heteroatom selected from a member of the group consisting of S, O, and N or a mixture, thereof; and wherein the reaction is carried out at temperatures varying from ambient to about 350° C. under ambient or autogenous pressure, in molar ratios of reactants which vary from equimolar to more than molar to less than molar for a time sufficient to obtain the desired additive product of reaction.

* * * * *